United States Patent
Sun et al.

(10) Patent No.: US 8,579,952 B2
(45) Date of Patent: Nov. 12, 2013

(54) MULTIFUNCTIONAL LASER THERAPEUTIC APPARATUS

(75) Inventors: Wen Sun, Wuhan (CN); Zhangqun Ye, WuHan (CN); Guohong Peng, WuHan (CN); Yongli Xue, Wuhan (CN); Honggen Wang, WuHan (CN); Wu Luo, WuHan (CN); Shougang Yu, WuHan (CN); Ding Li, WuHan (CN); Zhonghuan Song, WuHan (CN); Junhong Zhang, WuHan (CN)

(73) Assignee: Wuhan Miracle Laser Co., Ltd, Hubei (CN)

( * ) Notice: Subject to any disclaimer, the term of this patent is extended or adjusted under 35 U.S.C. 154(b) by 0 days.

(21) Appl. No.: 13/138,307

(22) PCT Filed: Jul. 15, 2010

(86) PCT No.: PCT/CN2010/001064
§ 371 (c)(1),
(2), (4) Date: Oct. 11, 2011

(87) PCT Pub. No.: WO2011/072472
PCT Pub. Date: Jun. 23, 2011

(65) Prior Publication Data
US 2012/0029604 A1    Feb. 2, 2012

(30) Foreign Application Priority Data

Dec. 14, 2009   (CN) .......................... 2009 1 0258792

(51) Int. Cl.
*A61N 5/067*    (2006.01)

(52) U.S. Cl.
USPC ................................... 607/89; 607/88; 606/3

(58) Field of Classification Search
USPC ............... 607/88–93, 138, 143; 606/2, 2.5, 3, 606/7–18
See application file for complete search history.

(56) References Cited

U.S. PATENT DOCUMENTS

| 5,139,494 A * | 8/1992 | Freiberg | 606/3 |
|---|---|---|---|
| 6,159,203 A * | 12/2000 | Sinofsky | 606/7 |
| 6,908,461 B2 * | 6/2005 | Momiuchi et al. | 606/10 |
| 2004/0133191 A1 * | 7/2004 | Momiuchi et al. | 606/10 |
| 2007/0179484 A1 * | 8/2007 | Sade | 606/10 |

FOREIGN PATENT DOCUMENTS

| CN | 1704028 A | 12/2005 |
|---|---|---|
| CN | 101273915 A | 1/2008 |
| CN | 201108497 Y | 9/2008 |

* cited by examiner

*Primary Examiner* — Ahmed Farah
(74) *Attorney, Agent, or Firm* — Jonathan E. Grant; Grant Patent Services

(57) ABSTRACT

A laser therapeutic apparatus includes a 532 nm wavelength laser or a 2000 nm wavelength thulium laser, a 980 nm wavelength laser or a 1470 nm wavelength laser, and a 2100 nm wavelength laser; an optical coupling device located at laser emitting ends of the above-mentioned lasers, which is used for coupling the lasers emitted from the above-mentioned lasers into the same optical fiber (1, 7, 11) to emit; and a control device capable of controlling the working modes of the above-mentioned lasers for laser emitting and the energy of the lasers emitted from the above-mentioned lasers.

3 Claims, 3 Drawing Sheets

MULTIFUNCTIONAL LASER THERAPEUTIC APPARATUS

FIELD OF THE INVENTION

The present invention relates to a laser therapeutic apparatus, and specifically to a multifunctional laser therapeutic apparatus.

BACKGROUND OF THE INVENTION

In the 1970s, the birth of laser medicine opened up new avenues for the study of occurrence, development of life sciences and diseases, and also provided novel means for clinical diagnosis and therapy of diseases. Laser medicine is capable to treat hundreds kinds of diseases. In one aspect, Urology Surgery has become the most active, and the fastest growing field of laser medicine technology. In addition, laser therapy of malignant tumors has made significant progress in clinically. According to the figures in the developed countries, an average of 10-15% application rate of laser surgical instruments is in the surgical operation, and ⅔ outpatient institutions in the United States have installed the laser medical equipment. The new-generation laser medical devices, including high-power holmium laser, green laser, semiconductor laser, and thulium laser, have demonstrated superior clinical features. However, single-wavelength laser inevitably encounters the advantages and disadvantages, for instance, green laser is superior in incision, vaporization, but with the larger postoperative missing tissue area in the incisional laser surgery of prostate; semiconductor laser has poor penetrability of water. Therefore, the super platform of multi-wavelength laser combined therapy has made a great figure. Chinese Pat. No. CN101273915A discloses a laser lithotripsy apparatus, comprising the functions of two different kinds of laser devices resolving the problems of equipment replacement in surgery, but unable to overcome the limitations of application range. For example, in one aspect, it does not provide technical solutions for the therapy of lithiasis with polyps; in a further aspect, it does not provide technical solutions for the therapy of benign prostatic hyperplasia, urinary stricture incision tissue, herniated disk, malignant tumor and other major diseases.

SUMMARY OF THE INVENTION

In view of the above-described problem, it is one objective of the present invention advantageously provides a multifunctional laser therapeutic apparatus, featured with wide application range, switching between different wavelengths of the laser according to different diseases and different therapy requirements, either using a single-wavelength laser, or combination therapy using a variety of wavelengths of laser; additionally, the present invention is able to change the working modes for laser emitting and adjust the laser emitting energy in accordance with the patient's conditions.

To achieve the above objective, the present invention provides the following technical solutions:

The invention presents a multifunctional laser therapeutic apparatus, comprising a laser with the wavelength of 532 nm or a thulium laser with the wavelength of 2000 nm, a laser with the wavelength of 980 nm or a laser with the wavelength of 1470 nm, and a laser with the wavelength of 2100 nm; comprising a optical coupling device is connected to the laser emitting ends of the above-described laser, which is used to couple the emitting laser by the above-described laser to the same optical fiber; comprising a control device to control the working modes for emitting laser, and the control device to control the emitting laser energy of the above-described laser, which is respectively connected with the above-described laser.

Wherein, the optical coupling device as described comprises three focus lenses, three optical fibers and an optical fiber. One ends of those three optical fibers as described are located in once side of those three focus lenses as described respectively for receiving the laser; while the other ends of those three optical fibers as described are connected with the fiber sintering by virtue of sintering to integrate, for coupling the three-beam laser into an optical fiber output.

Wherein, the optical coupling device as described comprises three focus lenses, three optical fibers, crystal tapered rod, an optical fiber, and shell. One ends of those three optical fibers as described are located in once side of those three focus lenses as described respectively for receiving the laser; while the other ends of those three optical fibers as described are tightly fit with the bottom surface of the crystal tapered rod respectively, the an optical fiber as described is connected with the top surface of the crystal tapered rod by sintering, and the three optical fibers, crystal tapered rod, a optical fiber as described are consolidated inside the shell with glue.

Wherein, the optical coupling device as described comprises three beam collimation devices, three reflection/transmission lens, a focusing lens, and an optical fiber. Those three reflection/transmission lenses are located in one end of the optical path of those three beam collimation devices, the focusing lens as described is located in one end of one of those three reflection/transmission lenses, and the an optical fiber as described is located in one end of a focusing lens.

Wherein, the control device as described comprises the control system, information sampling circuit, driver circuit, and display operator interface. Wherein, the control system is connected with the information sampling circuit, driver circuit, and display operator interface, which is used to receive the signals from the display operator interface and the information sampling circuit, and control the drive circuit. The control system is used to the refrigerating system, electricity supply system of the laser with the wavelength of 532 nm or the thulium laser with the wavelength of 2000 nm, the laser with the wavelength of 980 nm or the laser with the wavelength of 1470 nm, and the laser wavelength of 2100 nm. The information sampling circuit as described is connected with the laser power supplies of the laser with the wavelength of 532 nm or the thulium laser with the wavelength of 2000 nm, the laser with the wavelength of 980 nm or the laser with the wavelength of 1470 nm, and the laser wavelength of 2100 nm, respectively, used to collect the signals of the laser power supplies. The drive circuit as described is connected with the laser power supplies of the laser with the wavelength of 532 nm or the thulium laser with the wavelength of 2000 nm, the laser with the wavelength of 980 nm or the laser with the wavelength of 1470 nm, and the laser wavelength of 2100 nm, respectively, used to control the above-mentioned laser power supplies in accordance with the instructions of the control system, so as to control the working modes for emitting laser and the emitting laser energy of the above-described laser. The display operator interface as described is used to input the control signals and display the operating condition and operating parameters of the laser.

As a result of the application of the aforesaid technical solutions, the present invention has the advantages:

1. The present invention couples the laser with three kinds of wavelengths to an optical fiber by virtue of the optical coupling device, which is able to switch between different wavelengths of laser in accordance with the different diseases and different therapy requirements, either using a single-wavelength laser, or combination therapy using a variety of wavelengths of laser.

2. The present invention is able to change the mode f operation of laser emitting in accordance with the requirements of patient's conditions, which is capable of emitting the laser in a continuous, quasi-continuous, pulse and combination mode.

3. The present invention is able to adjust the laser emitting energy in accordance with the requirements of patient's conditions that is capable of adjusting the energy emitting of those three lasers in accordance with different proportions.

4. The present invention has a wide range of application, convenient to use, which could reduce the therapy costs of laser therapeutic apparatus, improve the therapy efficiency, avoid damage caused by the laser therapy and can solve the hospital's demand for the therapy of many diseases with a smaller investment.

Where: 1—optical fiber; 2—focusing lens; 3—optical fiber; 4—crystal tapered rod; 5—optical fiber; 6—shell; 7—optical fiber; 8—beam collimation device; 9—reflection/transmission lens; 10—focusing lens; and 11—optical fiber.

MODE OF CARRYING OUT THE INVENTION

The following examples are presented for the purpose of better understanding of this invention, rather than limitation of this invention.

Figure 1:
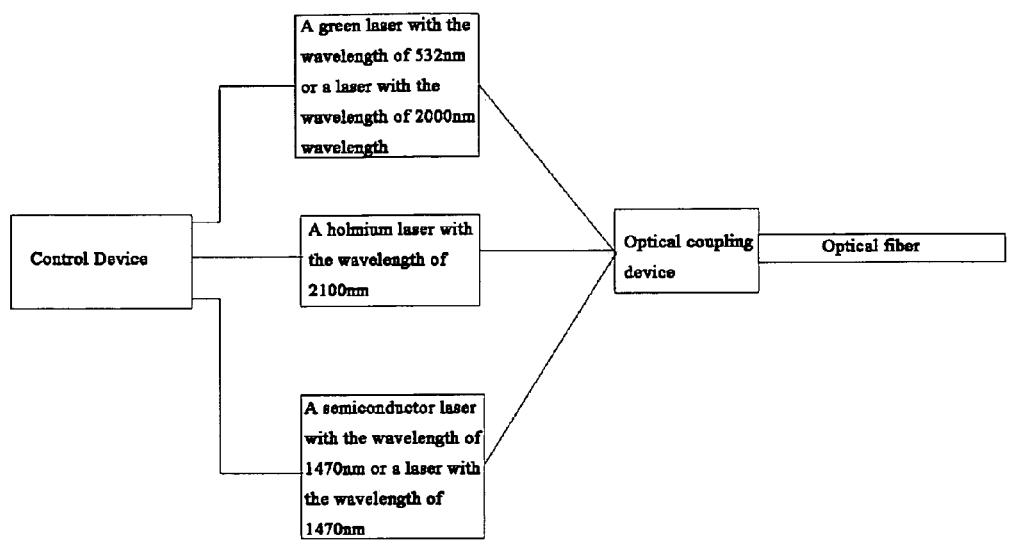
FIG. 1 is a schematic diagram of the overall structure of the present invention.

As shown in FIG. 1, the present invention relates to a multifunctional laser therapeutic apparatus, comprising:

1. A laser with the wavelength of 532 nm or a thulium laser with the wavelength of 2000 nm, a laser with the wavelength of 980 nm or a laser with the wavelength of 1470 nm, and a laser with the wavelength of 2100 nm;

2. A optical coupling device is connected to the laser emitting ends of the above-described laser, which is used to couple the laser emitting by the above-described laser to the same fiber;

3. A control device to control the working modes for emitting laser, and the control device to control the emitting laser energy of the above-described laser, which is respectively connected with the above-described laser.

Figure 5:
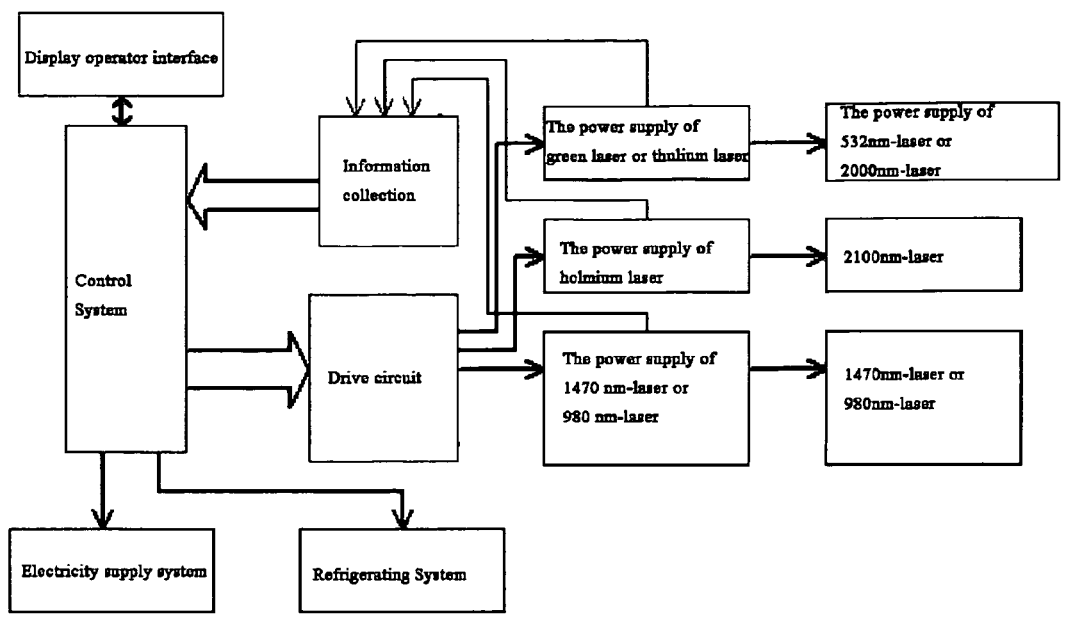
FIG. 5 is a block diagram of the control device of the present invention.

As shown in FIG. 5, the control device as described in this invention comprises the control system, information sampling circuit, driver circuit, and display operator interface. Wherein, the control system is connected with the information sampling circuit, driver circuit, and display operator interface, which is used to receive the signals from the display operator interface and the information sampling circuit, and control the drive circuit. The control system is used to the refrigerating system, electricity supply system of the laser with the wavelength of 532 nm or the thulium laser with the wavelength of 2000 nm, the laser with the wavelength of 980 nm or the laser with the wavelength of 1470 nm, and the laser wavelength of 2100 nm. The information sampling circuit as described is connected with the laser power supplies of the laser with the wavelength of 532 nm or the thulium laser with the wavelength of 2000 nm, the laser with the wavelength of 980 nm or the laser with the wavelength of 1470 nm, and the laser wavelength of 2100 nm, respectively, used to collect the signals of the laser power supplies. The drive circuit as described is connected with the laser power supplies of the laser with the wavelength of 532 nm or the thulium laser with the wavelength of 2000 nm, the laser with the wavelength of 980 nm or the laser with the wavelength of 1470 nm, and the laser wavelength of 2100 nm, respectively, used to control the above-mentioned laser power supplies in accordance with the instructions of the control system, so as to control the working modes for emitting laser and the emitting laser energy of the above-described laser. The display operator interface as described is used to input the control signals and display the operating condition and operating parameters of the laser.

Specific control process is as follows:

This invention is to control the working modes for emitting laser and laser emitting energy through the control of the laser power supplies of the three lasers.

On the display operator interface, Operators may pre-set the laser emitting power of those three lasers within the range as provided.

Control program will simultaneously control those three kinds of lasers to work in line with the e following three methods.

1. Drive the method procedures of the laser with the wavelength of 532 nm:

The Program will control the laser power supply of the laser with the wavelength of 532 nm to emit quasi-continuous laser according to the quasi-continuous requirements.

2. Drive the method procedures of the laser with the wavelength of 2100 nm:

The Program will control the laser power supply of the laser with the wavelength of 2100 nm to emit continuous pulsed laser light with optional 5-20 HZ adjustable pulse width according to the requirements of the laser.

3. Drive the method procedures of the laser with the wavelength of 980 nm:

The Program will control the laser power supply of the laser with the wavelength of 980 nm to emit continuous 980 nm laser.

Control the laser power supply of the laser with the wavelength of 1470 nm to emit continuous laser in the same control method.

The invention procedure will sample the operating conditions and malfunction information of each laser power supply, to ensure that each laser power supply is in the optimum condition by regulating the refrigeration system and electricity supply system.

Figure 2:
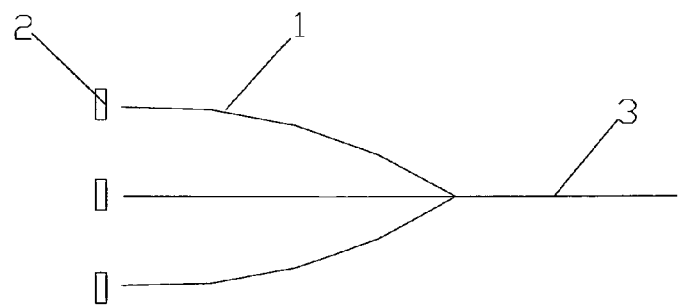
FIG. 2 is a schematic diagram of the optical coupling device Example 1 of the present invention.

As shown in FIG. 2, the optical coupling device Example 1 of the invention: the optical coupling device as described comprises three focus lenses, three optical fibers and an optical fiber. One ends of those three optical fibers as described are located in once side of those three focus lenses as described respectively for receiving the laser; while the other ends of those three optical fibers as described are connected with the fiber sintering by virtue of sintering to integrate, for coupling the three-beam laser into an optical fiber output.

Figure 3:
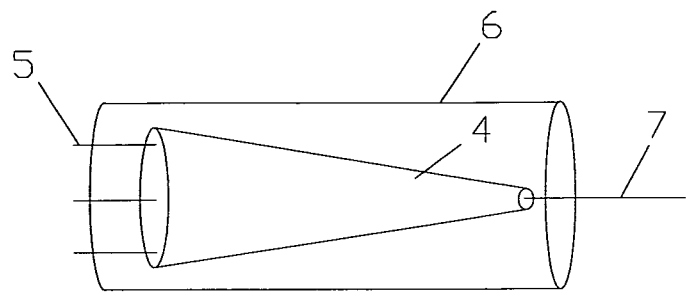
FIG. 3 is a schematic diagram of the optical coupling device Example 2 of the present invention.

As shown in FIG. 3, the optical coupling device Example 2 of the invention: the optical coupling device as described comprises three focus lenses, three optical fibers, crystal tapered rod, a optical fiber, and shell. One ends of those three optical fibers as described are located in once side of those three focus lenses as described respectively for receiving the laser; while the other ends of those three optical fibers as described are tightly fit with the bottom surface of the crystal tapered rod respectively, the an optical fiber as described is connected with the top surface of the crystal tapered rod by sintering, and the three optical fibers, crystal tapered rod, a optical fiber as described are consolidated inside the shell with glue.

Figure 4:
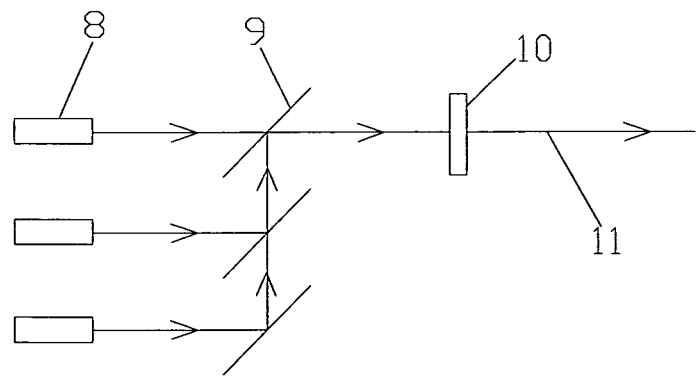
FIG. 4 is a schematic diagram of the optical coupling device Example 3 of the present invention.

As shown in FIG. 4, the optical coupling device Example 3 of the invention: the optical coupling device comprises three beam collimation devices, three reflection/transmission lens, a focusing lens, and an optical fiber. Those three reflection/transmission lenses are located in one end of the optical path of those three beam collimation devices, the focusing lens as described is located in one end of one of those three reflection/transmission lenses, and the an optical fiber as described is located in one end of a focusing lens.

The lasers used in the examples of this invention as follows:

1) The lasers used in this invention comprise a laser with the wavelength of 532 nm, a laser with the wavelength of 980 nm, and a laser with the wavelength of 2100 nm.

2) The lasers used in this invention comprise a laser with the wavelength of 532 nm, a laser with the wavelength of 1470 nm, and a laser with the wavelength of 2100 nm.

3) The lasers used in this invention comprise a thulium laser with the wavelength of 2000 nm, a laser with the wavelength of 980 nm, and a laser with the wavelength of 2100 nm.

4) The lasers used in this invention comprise a thulium laser with the wavelength of 2000 nm, a laser with the wavelength of 1470 nm, and a laser with the wavelength of 2100 nm.

For comparison, the performance of the present invention is described below:

1. Tumor Resection and Vaporization

Malignant tumor has become one of the most serious diseases threat to human life, and there is more than 4.50 million tumors patients in China at present. Wherein, the incidence of superficial bladder tumors ranks in the 4$^{th}$ of all male tumors, and ranks in the 9$^{th}$ of all female tumors.

In accordance with the clinical trial results, it demonstrates that holmium laser could properly resect the bladder tumors, kidney tumors, ureter, urethra tumors, papilloma, upper urinary tract tumors, and intracranial tumours, while its recurrence rate is lower than the traditional resection methods.

Green laser and semiconductor laser can also properly accomplish the resection and vaporization of bladder tumors.

By virtue of the invention, combined with the unique properties of holmium laser, green laser and semiconductor laser, to carry emitting surgery on urinary tract tumors combined with clinical therapy, it is able to improve the success rate of tumor surgical therapy.

2. Photodynamic Therapy of Malignant Tumors

Currently, semiconductor laser photodynamic therapy has been extensively applied in clinics for the treatment of superficial malignant tumors.

The principle of photodynamic tumor therapy method is to transmit the material molecules (photosensitizer) that can absorb light to the target cells, after the irradiation of appropriate wavelength of lights, activated to generate active oxygen substance, so as to impel the death of cells in the form of apoptosis or necrosis.

It has proposed up to dozens of photodynamic tumor therapy methods, including esophageal tumors, lung tumors, brain tumors, head and neck tumors, eye tumors, pharyngeal tumors, breast tumors, breast tumors, pleural mesothelioma, peritoneal sarcoma, bladder tumors, gynecological tumors, rectal tumors, and skin tumors and so on.

Compared with the traditional surgery, radiotherapy and chemotherapy methods, photodynamic therapy method has the advantages of very small trauma, low toxicity, good selectivity, superior applicability, repeatable therapy, palliative therapy, co-operation with surgery to improve the efficacy, eliminate hidden tumors lesions; protect the appearance and function of vital organs and so on.

Testing shows that the semiconductor laser is extremely useful for photodynamic therapy method, and the price photosensitizer suitable for this band is relatively cheap.

By virtue of semiconductor laser with the wavelength of 980 nm and green laser with the wavelength of 532 nm provided in this invention, green laser vaporization and semiconductor laser photodynamic therapy method can be combined for the therapy of non-muscle invasive bladder tumors. After the vaporization of green laser, and then exposed with the PDT, kill all remaining tumors and unfound small satellite-like tumors, which can reduce the recurrence rate and improve the efficacy.

3. The Comparison of Several Benign Prostatic Hyperplasia Surgeries

|  | Degree of normal tissue damage | Efficacy of surgery |
| --- | --- | --- |
| TU | Large, deep of thermal coagulation layer | Relatively fast resection speed, but more bleeding, blurred vision, or even blind to operate, may occur water intoxication and death |
| Green Laser | Small, approx. 1-2 mm damaged-layer | Excellent vaporization effect, less bleeding, clear vision, rapid for the blood-rich glands, while slow for the fibrosis and large glands |
| Holmium laser | Small, approx. 0.8 mm | Good resection hemostasis effect, clear vision, and the glands should be discharged after being resected to pieces |
| Semi-conductor Laser | Small, approx. 0.8 mm | Good tissue ablation capacity and hemostasis, but slow |

The above-mentioned semiconductor lasers include a laser with the wavelength of 1470 nm or a laser with the wavelength of 980 nm.

The above-mentioned green laser with the wavelength of 532 nm, the semiconductor laser with the wavelength of 980 nm or the semiconductor laser with the wavelength of 1470 nm, and the holmium laser with the wavelength of 2100 nm are coupled to an optical fiber, which are adjusted and regulated by virtue of controlling the working modes for laser emitting and the laser emitting energy, so as to give full play to the advantages of each laser, and overcoming the shortcoming of each laser.

4. The Comparison of Lithiasis with Polyps

| Lithotripsy Name | Features | Defects |
| --- | --- | --- |
| 1) Pharmacotherapy | Has its indications and cure efficiency, with good efficacy to the uric acid stones | Non-single therapy method, often need endoureteral lithotripsy. |
| 2) ESWT 3) EHDA, TUPL, and | Traditional means of endoureteral | May damage the tissue, the operation is not easy, and |

-continued

| Lithotripsy Name | Features | Defects |
| --- | --- | --- |
| UL | lithotripsy has its indications. | multiple complications. |
| 4) Dual-wavelength laser | Good efficacy of lithotripsy, inexpensive equipment and safe operation. | Low efficiency of cosine stones. |
| 5) Holmium laser | Able to crush the stones with various chemical compositions, with high efficiency of Lithotripsy. | The risk of injury ureter wall. |

Solid lumps formed in the cavity of human body catheter cavity or lumen organs (such as the kidney, ureter, gallbladder, or bladder, etc.), are found mainly in the gallbladder and bladder, renal pelvis, also found in the pancreatic ducts, salivary gland ducts and other cavities, which may cause lumen obstruction, affect the discharge of involved organs' liquid, resulting in pain, bleeding or infection or other symptoms. Lithiasis is comprised by inorganic salts or organic matters.

Holmium laser has excellent efficiency of lithotripsy, which is considered the optimum light source of endoureteral lithotripsy, but in accompany with the elimination of stones with polyps, it shall note the risk presence of injury ureter wall.

By virtue of this invention, for the therapy of stone with polyp disease, it should vaporize the polyps with green laser, and then implemented by the holmium laser for lithotripsy, which could make satisfactory effects.

5. Laser Therapy of Other Urological Diseases

Internal incision of urethral stricture;
Ureteral polyp surgery;
Penile tumor surgery;
Penis circumcision surgery;
Condyloma acuminatum surgery;
Internal incision of bladder neck stenosis;
Internal incision of pyeloureteric junction stricture;
Internal incision therapy of congenital megaureter;
Internal incision of ureteral intestinal stricture after ureteral urinary diversion;
Laser incision of pediatric ureterocele;
Internal incision of calyceal infundibular stricture;
Incision of urethral stricture after the snodgrass urethroplasty for hypospadias;
Urinary cyst decompression surgery and so forth Testing shows that the holmium laser is able to properly conduct the above-mentioned urinary tract surgery in clinics, but prone to lead the ureteral wall damage in the incision of ureteral strictures; however, the green laser is able to properly accomplish the vaporization therapy of ureteral strictures, its security is better than holmium laser. The therapeutic apparatus proposed in this invention can solve this problem.

6. Intervertebral Disc Herniation

Currently, there are more than 30 million intervertebral disc herniation patients in China.

Percutaneous Endoscopic Lumbar Discectomy, called as PELD.

Semiconductor laser and holmium laser can be implemented with the Percutaneous Endoscopic Lumbar Discectomy (PELD)

Compared with traditional surgical methods, PLDD has the advantages of shorter surgical time (usually within 1 h), smaller surgical damage, will not form the scar adhesions, can be carried output under local anesthesia in an outpatient, rapid postoperative recovery, without affecting the repeated open surgery, save costs and so forth.

| Therapy method | Conservative Therapy | | | | Surgical Therapy | | Minimally Invasive Laser Therapy |
| --- | --- | --- | --- | --- | --- | --- | --- |
| | Three-dimensional traction | Laser knife | Shock wave | Liquid knife | Conventional surgery | Internal fixation | PLDD (Percutaneous Laser Disc Decompression) |
| Indications | Narrow, mild, incipient patients | | | | Widely | Strict | Relatively wide |
| Hospitalization | Not necessarily | | | | Yes | Yes | Not necessarily |
| Curative effect | 70% | | | | 90% | 90% | 98% |
| Recurrence rate | 30% | | | | 3% | 3% | Not easy for recurrence |
| Security | High | | | | Risky | Risky | Very high |
| Acceptability | Easily accepted | | | | Scruple | Full of scrupulosities | Non surgery, easy to accept |
| Clinotherapy | Generally disuse | | | | 1-2 weeks | 2-3 weeks | 3-5 days |
| Complication | Non | | | | Slightly | Slightly | Non |
| Costs | Long-term costs and uncertain | | | | Higher | Higher | One-time therapy, and lower cost |

7. The Invention can Also be Used for Other Diseases

The holmium laser can be used for: Neurosurgery: hydrocephalus (third ventricle fistula, end-plate gastrostomy), etc.; General Surgery: surgical scalpel.

The semiconductor laser can be used for: Vascular: phlebeurysma, and hemangioma; Gynecology: cervical erosion, pelvic inflammatory; stomatology, dentistry and ENT, etc.

Apparently, the afore-mentioned examples are presented for the purpose of better illustrating the embodiments of this invention, rather than limitation of this invention. For common technicians in the corresponding areas, changes or modifications may be made on the basis of the above-described illustration in different forms. Herein cannot be exhaustive of all the operation modalities. Any obvious changes or modifications derived from the technical program of this invention are still in the scope of the invention.

The invention claimed is:

1. A multifunctional laser therapeutic apparatus comprising:
   a) a first laser, said first laser selected from the group consisting of a laser with the wavelength of 532 nm and a thulium laser with the wavelength of 2000 nm;
   b) a second laser, said second laser selected from the group consisting of a laser with the wavelength of 980 nm, and a laser with the wavelength of 1470 nm;
   c) a third laser, said third laser having the wavelength of 2100 nm;
   d) an optical coupling device comprising:
      i) three focus lenses, each of said of said focus lenses comprising:
         A) a first side; and
         B) a second side, each of said three focus lenses positioned so as to focus emitted laser energy from a specific one of said laser selected from the group of said first laser, said second laser and said third laser;
      ii) crystal tapered rod, said crystal tapered rod comprising:
         A) a top section; and
         B) a bottom section;
      iii) three optical fibers, each of said optical fibers comprising:
         A) a first end; and
         B) a second end;
         wherein said first end of each of the three said optical fibers are positioned at the second side of one of the three focus lenses and the second end of each of the three said optical fibers are tightly fit with the bottom surface of the crystal tapered rod;
      iv) a fourth optical fiber, an end of said fourth optical fiber being connected with the top surface of the crystal tapered rod; and
      v) a casing,
         wherein said crystal tapered rod is positioned inside said casing, said three optical fibers as described are connected within said casing to said crystal tapered rod, and wherein said fourth optical fiber is positioned downstream from said three optical fibers and distal to said crystal tapered rod such that the fourth optical fiber emerges distally outside of said casing; and
   e) a control device to control working modes for the emitting lasers, thereby controlling the emitted laser energy of the lasers, said control device connected to said lasers.

2. A multifunctional laser therapeutic apparatus as claimed in claim 1, said control device further comprising:
   a) a refrigerating system for the lasers;
   b) an electrical supply system;
   c) a control system, said control system used to control the refrigerating system and the electrical supply system;
   d) an information sampling circuit connected to the lasers, used to collect information on laser power supplies;
   e) a driver circuit, used to control said laser power supplies in accordance with output signals from the control system; and
   f) display operator interface, the display operator interface being used to input control signals and display operating condition and operating parameters of the laser.

3. A multifunctional laser therapeutic apparatus comprising:
   a) a first laser, said first laser selected from the group consisting of a laser with the wavelength of 532 nm and a thulium laser with the wavelength of 2000 nm;
   b) a second laser, said second laser selected from the group consisting of a laser with the wavelength of 980 nm, and a laser with the wavelength of 1470 nm;
   c) a third laser, said third laser having the wavelength of 2100 nm;
   d) an optical coupling device comprising:
      i) three beam collimation devices;
      ii) three reflection/transmission lenses, which focus the three beams of said emitted laser energy as a single beam;
      iii) a focusing lens to focus the beam of said single beam; and
      iv) an optical fiber through which said single beam passes; and
   e) a control device to control working modes for emitting lasers, thereby controlling the emitted laser energy of the lasers, said control device connected to said lasers.

* * * * *